United States Patent [19]
Pickenhagen et al.

[11] Patent Number: 5,892,062
[45] Date of Patent: Apr. 6, 1999

[54] CYCLIC CEDRENE ACETALS, THEIR PREPARATION AND THEIR USE

[75] Inventors: Wilhelm Pickenhagen, Höxter; Dietmar Schatkowski, Stadtoldendorf, both of Germany

[73] Assignee: Dragoco Gerberding & Co. AG, Germany

[21] Appl. No.: 19,249

[22] Filed: Feb. 5, 1998

[30] Foreign Application Priority Data

Feb. 6, 1997 [DE] Germany .................. 197 04 484.0

[51] Int. Cl.$^6$ .......................... C07D 317/70; A61K 7/46
[52] U.S. Cl. ........................ 549/432; 512/12; 512/13
[58] Field of Search .................. 549/432; 512/12, 512/13

[56] References Cited

U.S. PATENT DOCUMENTS 4,162,255  7/1979  Madaus et al. .................. 549/432

OTHER PUBLICATIONS

Takakura et al, Tetrahedron Letters, vol. 37(23), pp. 4043–4046, 1996.

*Primary Examiner*—Ba K. Trinh
*Attorney, Agent, or Firm*—Pendorf & Cutliff

[57] ABSTRACT

Cyclic cedrene acetals of the general formula A are described, in which the wavy lines represent the α- and β-configurations, and R and $R_1$ are the radicals below:

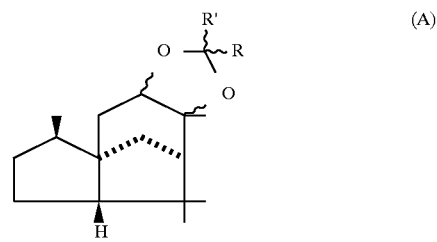

$R=R_1=H$
$R=H, R_1=Me/R=Me, R_1=H$
$R=H, R_1=Et/R=Et, R_1=H$
$R=H, R_1=Pr/R=Pr, R_1=H$
$R=H, R_1=Bu/R=Bu, R_1=H$
$R=H, R_1=Iso-Bu/R=Iso-Bu, R_1=H$
$R=H, R_1=Pentyl/R=Pentyl, R_1=H$
$R=H, R_1=Iso-Pentyl/R=Iso-Pentyl, R_1=H$
$R=H, R_1=Hexyl/R=Hexyl, R_1=H$
$R=R_1=Me\ (\alpha,\beta)$
$R=Me, R_1=Fl/R=Et, R_1=Me$
$R=R_1=Fl\ (\alpha,\beta)$
$R=Me, R_1=Pr/R=Pr, R_1=Me$
$R=Pt, R_1=Pr/R=Pr, R=Et$
$R=R_1=Cyclobutyl$
$R=R_1=Cyclopentyl$
$R=R_1=Cyclohexyl.$

3 Claims, No Drawings

CYCLIC CEDRENE ACETALS, THEIR PREPARATION AND THEIR USE

BACKGROUND OF THE INVENTION

Description

The strong odoriferous properties of animal secretions, glands and other organ components have fascinated man for thousands of years. Whilst originally the emanating perfumes were associated with magical powers and were thus used for religious and cultural purposes, there have been a variety of other uses, for example as medicaments, since ancient times. At the start of this century, ambergris, musk and civet appeared as valuable ingredients in perfumery. Thus, the first analytical work to determine the structure of the principal odoriferous substance in ambergris took place in the mid 1920s. The start of the 1930s then saw the first work on preparing it synthetically on an industrial scale. The growing demand for fragrances could no longer be met by products of natural, vegetable and animal origin. It is only possible to meet the growing demand for fragrances having improved properties, such as odor quality, stability in technical applications, skin tolerance, environmental compatibility and also adherence, through chemical synthesis of fragrances.

In order to achieve a steady eco balance, there is a desire for products which are on the one hand made, where possible, from renewable starting materials and, on the other are biodegradable. One such starting material of natural origin which is available in large quantities is cedrene, which is present in various types of cedar wood.

As long as two decades ago, a series of secondary products of -(α)-cedrene (1) was prepared and fragrance properties described. In his book "Riechstoff und Geruchsinn" [Fragrance and Sense of Smell] (Springer-Verlag, Berlin 1990, ISDN 3-540-52560-2, pages 170–172), G. Ohloff reports in summary that a series of commercial fragrances are derived from α-cedrene (1). In "Perfume and Flavor Chemicals" (No. 593–600, 602), S. Arctander describes several fragrances derived from cedrene.

The derivatives accessible from α-cedrene (1) by epoxidation, allyloxidation, esterification and etherification are sensorially desirable fragrances of the warm-woody odor type, some having an ambergris-type effect.

SUMMARY OF THE INVENTION

According to the above prior art, this field of fragrance chemistry has been investigated particularly well. In addition to some cedrene derivatives having fragrance properties, a larger number of derivatives of the said sesquiterpenes is known which have no or essentially no olfactory properties. For this reason, it is particularly surprising that, in the field of cedrene derivatives, it has been possible to find the novel compounds, described here, of the general formula A (in which the wavy lines represent the α- and β-configurations, and $R_1$ and $R_2$ are hydrogen or methyl, ethyl, propyl, butyl, isobutyl, pentyl, isopentyl, hexyl, isohexyl, cyclopentyl and cyclohexyl radicals), which have quite unique odoriferous properties and clearly stand out from and are superior to the known fragrances made from a α-cedrene (1). The cedrene derivatives of the general formula A have odor properties of the ambergris type and also have a radiating, powerful effect which intensifies quite different perfume notes and prolongs their perfume effect.

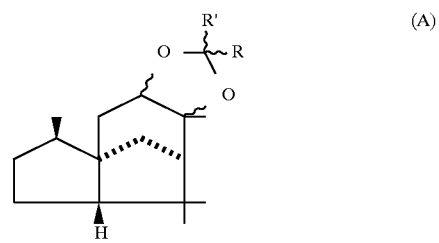

(A)

DETAILED DESCRIPTION OF THE INVENTION

To prepare the compound of the general formula A, (−)-α-cedrene (1) was converted in a known manner to (−)-α-cedrene epoxide (2) by treatment with peracetic acid (in Organileum, Organisch-Chemisches Grundpraktikum [Basic Practical Organic Chemistry], VEB Deutscher Verlag der Wissenschaften, Berlin, 1986, Order No. 5714576, page 568). The epoxide (2) obtained from cedrene was then converted in a known manner (Houben-Weyl) into a mixture of the epimeric diols (3), this diol mixture having varying isomer distributions and odor effects, depending on the production conditions. The structure was assigned on the basis of the NMR results.

The novel cyclic acetals of the general formula A are prepared from the diols 3, which were present in pure or in enriched form or as equilibrium mixture, in a manner known per se by reaction with aliphatic aldehydes and ketones with acid catalysis using various solvents, for example toluene, cyclohexane, naphtha fractions or diethyl ether.

Diagram 1

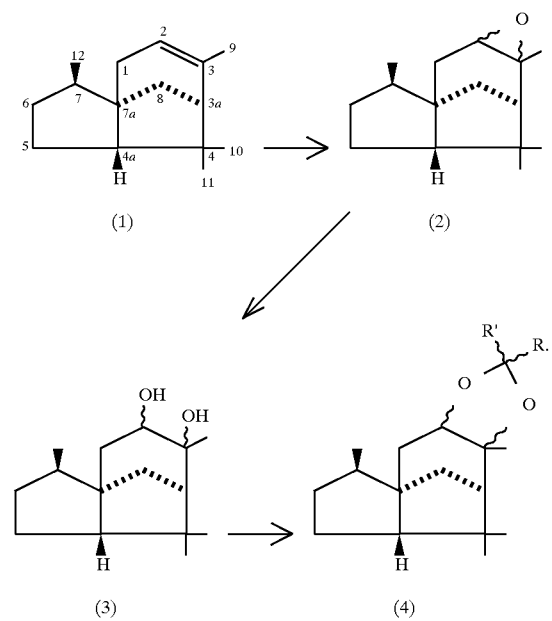

These epimerically pure epoxides 2a and 2b can be converted individually or as a mixture, depending on the production conditions, into the diastereomeric diols 3a–f. Depending on the chosen reaction conditions, the epimeric epoxides 2a and 2b can be produced in varying quantity ratios, so that after opening the epoxides to give the diastereomeric diols 3a/b/c/d/e/f/g/h, the latter are also present in varying quantity ratios. The stereochemical ratios in the reaction with the aldehydes and ketones remain essentially unchanged, so that the novel mixed acetals of the formula A are in this case in the form of diastereomeric mixtures.

The novel mixed acetals of formula A each have, in pure form and also as stereoisomeric mixtures, original fragrance properties and can advantageously be used, in pure form or as diastereomeric mixtures, as fragrances and constituents of perfume oils.

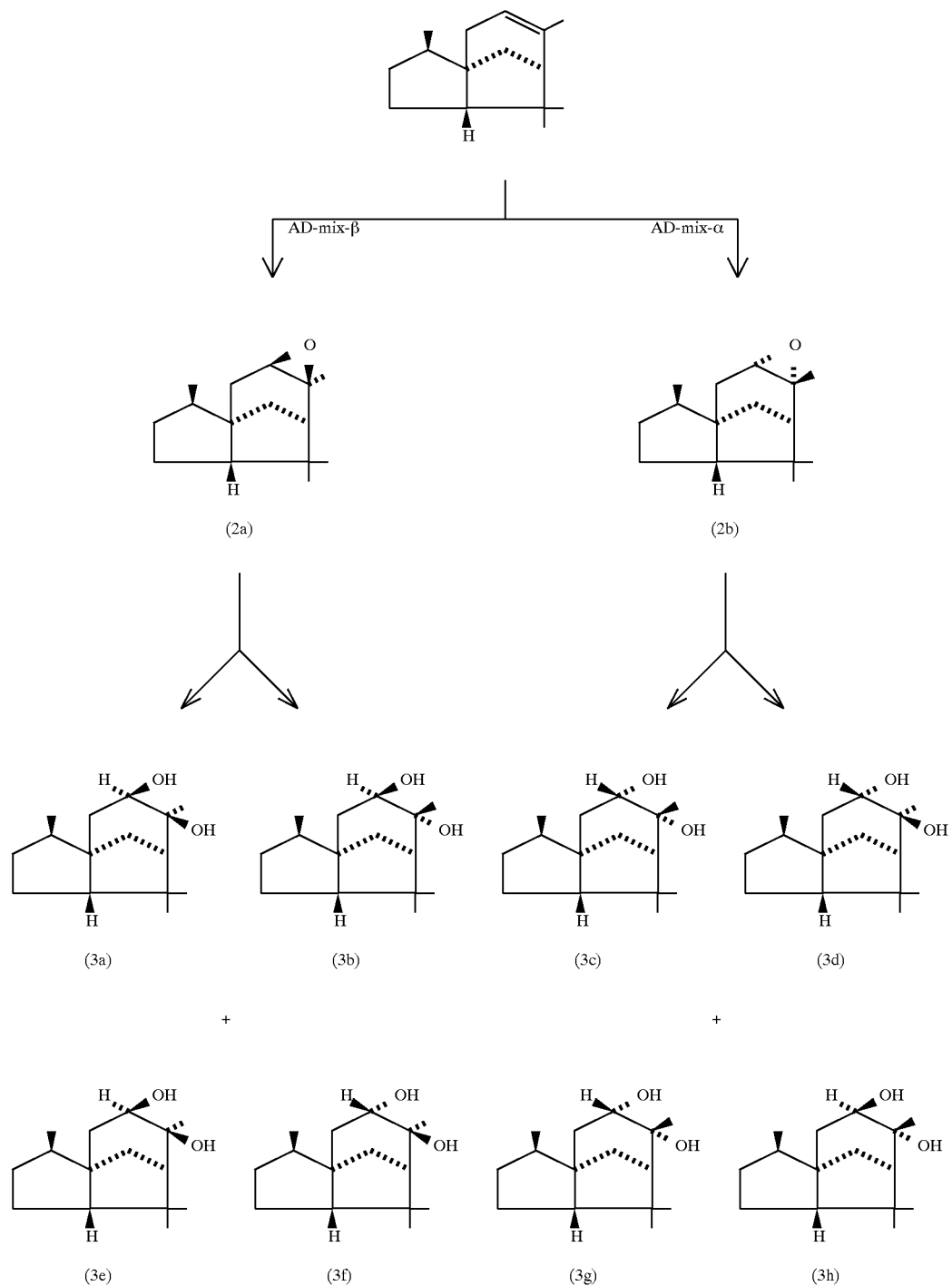

EXAMPLE 1
Preparation of (−)-α-cedrene epoxide (2)

500 g (2.00 mol) of (−)-α-cedrene (1) (82% by GC $[\alpha]_D=-75.8°$), 500 ml of diethyl ether and 100 g of sodium acetate were charged to a 2 l mixer fitted with reflux condenser, thermometer and dropping funnel, and then 430 g (2.20 mol) of 40% peracetic acid were added at 20–25° C. over the course of 1 h. After the dropwise addition was complete, the mixture was stirred for 2 h and then worked up. The organic phase was separated off, washed with soda solution and water until neutral, and dried over sodium sulfate and the solvent was distilled off under reduced pressure to give 526.5 g of crude product (78.2% by GC). Gas chromatogram (HP 5970 B, DBWAX-60 N, 60 m, 60° C.–240° C./min).

Distilling 100 g of crude product over a 15 cm Vigreux column gave 95 g of crude 2; b.p.: 115° C. to 138° C./2 mmHg, GC 2 (80.2%).

D 20/4: 1.0009
n20/D: 1.4965
[α]20/D: −72.4

EXAMPLE 2
Preparation of 2β-,3β-epoxycedrene (2a)—Diagram 2

50 ml of tert-butanol, 50 ml of water and 14 g of AD-mix-β (=0.01 mol olefin equivalent; Aldrich) were charged to a 250 ml mixer fitted with reflux condenser, thermometer and dropping funnel and stirred for 2 h at room temperature.

After this time, two phases had formed which clearly separated from one another. The lower phase was pale yellow. After this time, 0.95 g (0.01 mol) of methanesulfonamide was added to the stirred solution. The mixture was then cooled to 0° C. After one of the previously dissolved salts had precipitated out, 2.55 g (0.01 mol) of (−)-α-cedrene (2) (82.0% by GC) were added dropwise at 0° C. with vigorous stirring, and the mixture was stirred at this temperature for a total of 60 h. Aqueous sodium sulfite solution was then added to the reaction mixture, which was allowed to warm to room temperature and was stirred at this temperature for a further 1 h in total. After ether had been added to the mixture, the organic phase was separated off, the aqueous phase was extracted 3 times with 50 ml of diethyl ether in each case, and the combined organic phases were washed once with 10% KOH and once with water until neutral. The resulting composition was then dried over sodium sulfate and the solvent was distilled off under reduced pressure to give 1.9 g of crude product. GC 2a (78%).

EXAMPLE 3
Preparation of 2α-,3α-epoxycedrene (2b)—Diagram 2

50 ml of tert-butanol, 50 ml of water and 14 g of AD-mix-α (=0.01 mol olefin equivalent; Aldrich) were charged to a 250 ml mixer fitted with reflux condenser, thermometer and dropping funnel and stirred for a total of 1 h at room temperature. After this time, two phases had formed. The lower phase was pale yellow. A total of 0.95 g (0.01 mol) of methane-sulfonamide was then added to the stirred solution. The mixture was then cooled to 0° C. After one of the dissolved salts had precipitated out, 2.55 g (0.01 mol) of (−)-α-cedrene (2) (82.0% by GC) were added to this suspension at 0° C. with vigorous stirring, and stirring was continued at this temperature for a total of 72 h. After this time, aqueous sodium sulfite solution was added to the reaction mixture, which was allowed to warm to room temperature and was further stirred for a total of 1 h at room temperature and then worked up. After ether had been added to the mixture, the organic phase was separated off, the aqueous phase was extracted three times with 50 ml of diethyl ether in each case, and the combined organic phases were washed once with 10% KOH and once with water until neutral. The resulting reaction mixture was then dried over sodium sulfate and the solvent was distilled off under reduced pressure to give 1.8 g of crude product. GC 2b (84.1%).

EXAMPLE 4
Preparation of cedranediol mixture (3)—Diagram 1

2000 g of 10% sulfuric acid and 3 g of Aliquat R336 were charged to a 4 l three-necked flask fitted with reflux condenser, dropping funnel and thermometer. 300 g (1.09 mol) of (−)-α-cedrene epoxide (2) (80.2% by GC) from Example 2 were then added dropwise with vigorous stirring over the course of 10 minutes and the mixture was then stirred at 20–25° C. with vigorous stirring for a total of 48 h. The precipitated organic product was then filtered off and washed with 2% soda solution and water until neutral. 120 g of diol mixture (3) were separated off and then recrystallized from 2 l of cyclohexane. Filtering off the solvent with suction gave 98 g of crystalline cedranediol 3 (37.6% of theory).

m.p. 167–168° C.
GC: See Example 1 for conditions
3a, e, c, g: 49.3%
3b, f, d, h: 32.0%
GC/MS: HP 5970 B, DBWAX-60 N, 60 m, 60° C.–240° C., 4° C./min.
3a, e, c, g: $R_t$=55.60
MS: m/e (%)=238 (10, M$^+$), 223 (45), 205 (34), 193 (30), 167 (46), 121 (46), 107 (61), 99 (66), 81 (58), 43 (100).
3b, d, f, h: $R_t$=55.97
MS: m/e (%)=238 (10, M$^+$), 223 (38), 205 (29), 193 (20), 167 (34), 121 (44), 109 (37), 107 (40), 81 (46), 43 (100).

EXAMPLE 5
Reaction of cedranediol mixture 3 (from Diagram 1) with acetone 10.1 g (0.04 mol) of cedranediol mixture 3 (Diagram 1, from Example 4), 23.3 g (0.4 mol) of acetone, 100 ml of toluene and 0.2 g of p-toluene-sulfonic acid were stirred in a 250 ml mixer fitted with dropping funnel, thermometer and reflux condenser for a total of 24 h at 20–25° C. After this time, the product was washed once with 10 ml of 10% soda solution and once with 50 ml of water until neutral and dried over sodium sulfate and the solvent was distilled off under reduced pressure to give 10.7 g of crystalline crude product.

The crystalline crude product was recrystallized from 100 ml of acetoacetic ester. Filtering off the solvent with suction gave 5.6 g of a white, crystalline product.

GC (see Example 1 for conditions): 95.6%
m.p.: 157–158° C.
GC/MS: See Example 2 for conditions
$R_t$=41.43
MS: m/e (%)=278 (5, M$^+$), 263 (49), 221 (100), 203 (48), 161 (10), 147 (21), 133 (41), 119 (73), 105 (36), 69 (35), 43 (51).
$^{13}$C-NMR (CDCl$_3$), Varian VXR 300: δ [ppm]=15.42, 27.56, 28.74, 29.67, 30.26, 31.12 (CH$_3$), 25.42, 35.88, 38.51, 41.00 (CH$_2$), 41.92, 57.39, 58.58, 78.79 (CH), 42.43, 52.38, 84.99, 108.87 (C).

EXAMPLE 6
Reaction of cedranediol mixture 3 (from Diagram 1) with methyl ethyl ketone 10.1 g (0.04 mol) of cedranediol mixture 3 (from Example 4), 28.8 g (0.4 mol) of methyl ethyl ketone, 100 ml of toluene and 0.2 g of p-toluene-sulfonic acid were stirred in a 250 ml mixer fitted with dropping funnel, reflux condenser and thermometer for a total of 48 h at 20–25° C. After this time, the product was washed once with 10% soda solution and once with water until neutral and dried over sodium sulfate and the solvent was distilled off under reduced pressure to give 10.5 g of crude product.

GC (see Example 1 for conditions):

$R_t$=44.5=15.1%

$R_t$=45.4=19.1%

GC/MS (see Example 2 for conditions)

$R_t$=44.57

MS: m/e (%)=292 (3, M$^+$), 277 (4), 263 (34), 221 (100), 203 (49), 133 (45), 119 (82), 105 (40), 69 (40), 43 (50).

$R_t$=45.20

MS: m/e (%)=292 (2, M$^+$), 277 (2), 263 (35), 221 (100), 203 (52), 133 (43), 119 (76), 105 (38), 69 (37), 43 (50).

EXAMPLE 7
Reaction of cedranediol mixture 3 (from Diagram 1) with methyl propyl ketone 10.1 g (0.04 mol) of cedranediol mixture 3 (Diagram 1 from Example 4), 34.4 g (0.4 mol) of methyl propyl ketone, 100 ml of toluene and 0.2 g of p-toluene-sulfonic acid were stirred in a 250 ml mixer fitted with thermometer and reflux condenser at 20–25° C. for a total of 24 h. After this time, the product was washed once with 10% soda solution and once with water and dried over sodium sulfate and the solvent was distilled off under reduced pressure to give 10.2 g of a pale yellow, crystalline crude product.

GC (see Example 2 for conditions)

$R_t$=44.10=9.2%

$R_t$=44.68=17.7%

GC/MS: see Example 2 for conditions $R_t$=45.20

MS: m/e (%)=306 (2, M$^+$), 291 (3), 263 (33), 221 (100), 203 (41), 147 (19), 133 (38), 119 (68), 105 (34), 69 (35), 43 (52).

$R_t$=44.68

MS: m/e (%)=306 (1, M$^+$), 291 (1), 263 (31), 221 (100), 203 (45), 147 (19), 133 (39), 119 (70), 105 (34), 69 (34), 43 (50).

EXAMPLE 8
Reaction of cedranediol mixture 3 (Diagram 1) with diethyl ketone 10.1 g (0.04 mol) of cedranediol mixture 3 (Diagram 1 from Example 4), 34.4 g (0.4 mol) of diethyl ketone, 100 ml of toluene and 0.2 g of p-toluene-sulfonic acid were stirred in a 250 ml mixer fitted with reflux condenser and thermometer at 20–25° C. for a total of 24 h. After this time, the product was washed once with 10% soda solution and once with water and dried over sodium sulfate and the solvent was distilled off under reduced pressure to give 10.8 g of a pale brown, crystalline crude product.

GC (see Example 1 for conditions): 29.5%

GC/MS (see Example 2 for conditions)

$R_t$=44.61

MS: m/e (%)=306 (4, M$^+$), 291 (1), 277 (15), 221 (39), 203 (21), 177 (31), 159 (37), 119 (44), 91 (48), 69 (100), 41 (85).

EXAMPLE 9
Reaction of cedranediol mixture 3 (Diagram 1) with cyclopentanone 10.1 g (0.04 mol) of cedranediol mixture 3 (Diagram 1—from Example 4), 33.6 g (0.4 mol) of cyclopentanone, 100 ml of toluene and 0.2 g of p-toluenesulfonic acid were stirred in a 250 ml mixer fitted with reflux condenser and thermometer at 20–25° C. for 24 h. After this time, the product was washed once with 10% soda solution and once with 50 ml of water and dried over sodium sulfate and the solvent was distilled off under reduced pressure to give 10.5 g of a yellow, crystalline crude product.

GC (see Example 1 for conditions): 49.8%

GC/MS (see Example 2 for conditions)

$R_t$=49.92

MS: m/e (%)=304 (15, M$^+$), 275 (22), 221 (100), 205 (88), 133 (46), 119 (90), 105 (48), 69 (54), 55 (69), 41 (54).

EXAMPLE 10
Reaction of cedranediol mixture 3 (Diagram 1) with cyclohexanone 10.1 g (0.04 mol) of cedranediol mixture 3 (Diagram 1—from Example 4), 39.2 g (0.4 mol) of cyclohexanone, 100 ml of toluene and 0.2 g of p-toluenesulfonic acid were stirred in a 250 ml mixer fitted with reflux condenser and thermometer at 20–25° C. for 24 h. The product was then washed once with 10% soda solution and once with water until neutral and dried over sodium sulfate and the solvent was distilled off under reduced pressure to give 11.3 g of a pale yellow, crude product.

GC (see Example 1 for conditions): 73%

GC/MS (see Example 2 for conditions)

$R_t$=53.22

MS: m/e (%)=318 (22, M$^+$), 275 (24), 221 (100), 203 (63), 147 (25), 133 (52), 119 (91), 105 (49), 69 (68), 55 (66), 41 (61).

$^{13}$C-NMR (CDCl$_3$), Varian VXR-300: δ[ ppm]=15.45, 28.10, 28.71, 31.20 (CH$_3$), 24.11, 24.25, 25.17, 25.37, 35.78, 38.48, 38.92, 39.57, 41.71 (CH$_2$), 41.87, 57.40, 58.66, 78.21 (CH), 42.83, 52.42, 84.36, 109.83 (C).

EXAMPLE 11
Reaction of cedranediol mixture 3 (Diagram 1) with acetaldehyde 10.1 g (0.04 mol) of cedranediol mixture 3 (Diagram 1—from Example 4), 17.6 g (0.4 mol) of acetaldehyde, 100 ml of toluene and 0.2 g of p-toluenesulfonic acid were stirred in a 250 ml mixer fitted with reflux condenser and thermometer at 20–25° C. for a total of 3 h. After this time, the product was washed once with 10% soda solution and once with water and dried over sodium sulfate and the solvent was distilled off under reduced pressure to give 10.3 g of a pale crude product.

GC (see Example 1 for conditions): 37.8%, 60.08%

GC/MS (see Example 2 for conditions)

$R_t$=41.29

MS: m/e (%)=264 (19, M$^+$), 249 (43), 221 (18), 203 (77), 177 (65), 119 (100), 105 (61), 95 (58), 69 (71), 43 (100).

$R_t$=40.91

MS: m/e (%)=264 (36, M$^+$), 249 (49), 221 (24), 203 (83), 177 (30), 119 (91), 105 (57), 95 (60), 69 (69), 43 (100).

EXAMPLE 12
Reaction of cedranediol mixture 3 (Diagram 1) with propionaldehyde 10.1 g (0.04 mol) of cedranediol mixture 3 (Diagram 1—from Example 4), 23.2 g (0.4 mol) of propionaldehyde, 100 ml of toluene and 0.2 g of p-toluenesulfonic acid were stirred in a 250 ml mixer fitted with reflux condenser and thermometer at 20–25° C. for a total of 4 h. After this time, the product was washed once with 10% soda solution and once with water and dried over sodium sulfate and the solvent was distilled off under reduced pressure to give 11.2 g of a pale, crystalline crude product.

GC (see Example 1 for conditions): 25.7%, 62.3%
GC CMS (see Example 2 for conditions)
$R_t$=42.49
MS: m/e (%)=278 (20, M$^+$), 249 (31), 203 (100), 161 (15), 147 (32), 133 (63), 119 (97), 105 (53), 91 (24), 69 (54), 43 (37).

$R_t$=42.94
MS: m/e (%)=278 (4, M$^+$), 249 (33), 203 (100), 161 (15), 147 (33), 133 (64), 119 (98), 105 (54), 91 (24), 69 (54), 41 (42).

EXAMPLE 13

Reaction of cedranediol mixture 3 (Diagram 1) with butyraldehyde 10.1 g (0.04 mol) of cedranediol mixture 3 (Diagram 1—from Example 4), 28.8 g (0.4 mol) of butyraldehyde, 100 ml of toluene and 0.2 g of p-toluenesulfonic acid were stirred in a 250 ml mixer fitted with reflux condenser and thermometer at 20–25° C. for 6 h. After this time, the product was washed once with 10% soda solution and once with 50 ml of water and dried over sodium sulfate and the solvent was distilled off under reduced pressure to give 13.4 g of a pale crude product.

GC (see Example 1 for conditions): 26.3%, 63.7%
GC/MS (see Example 2 for conditions)
$R_t$=44.14
MS: m/e (%)=292 (1, M$^+$), 249 (28), 203 (100), 161 (14), 147 (31), 133 (64), 119 (98), 105 (51), 69 (55), 43 (42).

$R_t$=44.69
MS: m/e (%)=292 (3, M$^+$), 249 (29), 203 (100), 161 (13), 147 (31), 133 (59), 119 (89), 105 (47), 69 (54), 41 (44).

EXAMPLE 14

Reaction of cedranediol mixture 3 (Diagram 1) with isobutyraldehyde 10.1 g (0.04 mol) of cedranediol mixture 3 (Diagram 1 from Example 4), 28.8 g (0.4 mol) of isobutyraldehyde, 100 ml of toluene and 0.2 g of p-toluenesulfonic acid were stirred in a 250 ml mixer fitted with reflux condenser and thermometer at 20–25° C. for 5 h. After this time, the product was washed once with 10% soda solution and once with 50 ml of water and dried over sodium sulfate and the solvent was distilled off under reduced pressure to give 10.2 g of a pale crude product.

GC (see Example 1 for conditions): 30.68%, 61.32%
GC/MS (see Example 2 for conditions)
$R_t$=42.29
MS: m/e (%)=292 (1, M$^+$), 249 (31), 203 (100), 161 (13), 147 (29), 133 (55), 119 (87), 105 (43), 91 (17), 69 (42), 41 (29).

$R_t$=42.82
MS: m/e (%)=291 (5, M$^+$), 249 (28), 203 (100), 161 (13), 147 (29), 133 (57), 119 (89), 105 (46), 91 (17), 69 (43), 41 (32).

EXAMPLE 15

Reaction of cedranediol mixture 3 (Diagram 1) with valeraldehyde 10.1 g (0.04 mol) of cedranediol mixture 3 (Diagram 1—from Example 4), 34.4 g (0.4 mol) of valeraldehyde, 100 ml of toluene and 0.2 g of p-toluenesulfonic acid were stirred in a 250 ml mixer fitted with reflux condenser and thermometer at 20–25° C. for 7 h. After this time, the product was washed once with 10% soda solution and once with 50 ml of water and dried over sodium sulfate and the solvent was distilled off under reduced pressure to give 10.6 g of a pale crude product.

GC (see Example 1 for conditions): 43.91%, 16.67%
GC/MS (see Example 2 for conditions)
$R_t$=46.39
MS: m/e (%)=306 (1, M$^+$), 249 (27), 203 (100), 147 (31), 133 (59), 119 (85), 105 (47), 91 (24), 69 (52), 41 (46).

$R_t$=47.11
MS: m/e (%)=306 (3, M$^+$), 249 (31), 203 (100), 147 (26), 133 (53), 119 (77), 105 (38), 91 (16), 69 (42), 41 (34).

EXAMPLE 16

Reaction of cedranediol mixture 3 (Diagram 1) with isovaleraldehyde 10.1 g (0.04 mol) of cedranediol mixture 3 (not recrystallized), 34.4 g (0.4 mol) of isovaleraldehyde, 100 ml of toluene and 0.2 g of p-toluenesulfonic acid were stirred in a 250 ml mixer fitted with reflux condenser and thermometer at 20–25° C. for 4 h. After this time, the product was washed once with 10% soda solution and once with 50 ml of water and dried over sodium sulfate and the solvent was distilled off under reduced pressure to give 11 g of a colorless crude product.

GC (see Example 1 for conditions): 16.4%, 19.5%, 12.2%, 9.2%, 9.5%
GC/MS (see Example 2 for conditions)
$R_t$=44.49
MS: m/e (%)=306 (1, M$^+$), 249 (26), 203 (100), 161 (13), 147 (28), 133 (59), 119 (88), 105 (43), 69 (49), 41 (41).

$R_t$=45.1
MS: m/e (%)=306 (3, M$^+$), 249 (30), 203 (100), 147 (26), 133 (54), 119 (79), 105 (40), 69 (43), 41 (37).

$R_t$=46.60
MS: m/e (%)=306 (8, M$^+$), 291 (11), 263 (41), 220 (90), 203 (30), 177 (45), 150 (100), 121 (39), 69 (54), 43 (94).

$R_t$=48.47
MS: m/e (%)=306 (7, M$^+$), 291 (10), 263 (14), 220 (81), 203 (30), 177 (42), 150 (100), 121 (39), 69 (49), 43 (85).

$R_t$=48.80
MS: m/e (%)=306 (10, M$^+$), 291 (11), 263 (11), 220 (77), 203 (18), 177 (40), 150 (100), 121 (41), 69 (44), 43 (85).

EXAMPLE 17

Reaction of cedranediol mixture (3) (Diagram 1) with formaldehyde 30 g (1 mol) of p-formaldehyde, 200 ml of benzene and 3 g of conc. sulfuric acid were stirred in a 250 ml mixer fitted with reflux condenser and thermometer at 20–25° C. for 10 minutes initially. 5 g (0.019 mol) of cedranediol 3 (Diagram 1—from Example 4) were then added in portions over the course of 5 minutes. The mixture was then stirred at 20–25° C. over a period of 3 h. After the p-formaldehyde had been filtered off, the reaction mixture was washed once with 10% soda solution and once with water and dried over sodium sulfate, and the solvent was distilled off under reduced pressure to give 5.4 g of a colorless crude mixture.

GC (see Example 1 for conditions): 41.5%
GC/MS (see Example 2 for conditions)
$R_t$=42.20
MS: m/e (%)=250 (31, M$^+$), 235 (37), 204 (37), 161 (47), 149 (50), 119 (48), 107 (59), 100 (100), 69 (63), 43 (96).

EXAMPLE 18
Accord Muguet

| | |
|---|---:|
| Acetonid (from example 5) | 2 |
| Aldehyde C11 en 1% | 10 |
| Citronellyl acetate | 10 |
| Florindal (a) | 10 |
| cis-3-Hexenyl acetate 10% | 10 |
| Phenyl ethyl isobutyrate | 15 |
| cis-3-Hexenol 1% | 15 |
| Aldehyde C10 1% | 15 |
| Indole 10% | 20 |
| Phenyl ethyl dimethyl carbinol | 25 |
| Sandranol (a) | 25 |
| Geraniol | 35 |
| Aldehyde C9 1% | 40 |
| Hedione ® (b) | 60 |
| Linalol | 60 |
| Phenyl ethyl acetate | 60 |
| Lyral ® (c) | 70 |
| Benzyl acetate | 80 |
| Citronellol | 120 |
| Phenyl ethyl alcohol | 140 |
| Hexyl cinnamic aldehyde alpha | 178 |
| | 1000 |

(a) = DRAGOCO
(b) = Firmenich
(c) = IFF

Acetonid from example 5 improves diffusion and freshness of the top note, and increases the substantivity on the dry out.

EXAMPLE 19
Accord Jasmin

| | |
|---|---:|
| Acetonid (from example 5) | 1 |
| Methyloctincarbonate 1% | 5 |
| Aldehyde C16 10% | 5 |
| Kreosol 10% (a) | 5 |
| Dimethylanthranilate 10% | 5 |
| cis-3-Hexenol 10% | 5 |
| Indole | 5 |
| Aldehyde C18 | 5 |
| Phenoxyethylisobutyrate | 5 |
| Kresol para 10% | 10 |
| Maltol 1% | 10 |
| Eugenol | 10 |
| cis-3-Hexenylacetate 10% | 10 |
| Aldehyde C14 | 10 |
| Ethyl laurate | 10 |
| Methyl anthranilate 10% | 10 |
| Hedione ® (b) | 15 |
| Hexylbenzoate | 15 |
| Cycloamylone (a) | 20 |
| Linalol | 30 |
| Benzylalcohol | 50 |
| Lactoscaton (a) | 60 |
| Benzylbenzoate | 149 |
| Hexylcinnamic aldehyde alpha | 250 |
| Benzylacetate | 300 |
| | 1000 |

(a) = DRAGOCO
(b) = Firmenich

The use of Acetonid from example 5 increases the typical animalic, i.e. flowery indole note of jasmine, increases the diffusion and substantivity on the dry-out.

What is claimed is:

1. Cyclic cedrene acetals of the general formula A, in which the wavy lines represent α- and β-configurations, and R and R₁ are the radicals below:

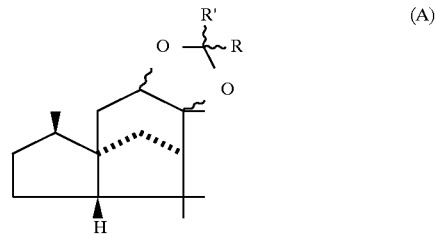

R=R₁=H
R=H, R₁=Me/R=Me, R₁=H
R=H, R₁=Et/R=Et, R₁=H
R=H, R₁=Pr/R=Pr, R₁=H
R=H, R₁=Bu/R=Bu, R₁=H
R=H, R₁=i-Bu/R=i-Bu, R₁=H
R=H, R₁=Pentyl/R=Pentyl, R₁=H
R=H, R₁=Isopentyl/R=Isopentyl, R₁=H
R=H, R₁=Hexyl/R=Hexyl, R₁=H
R=R₁=Me (α,β)
R=Me, R₁=Et/R=Et, R₁=Me
R=R₁=Et (α,β)
R=Me, R₁=Pr/R=Pr, R₁=Me
R=Et, R₁=Pr/R=Pr, R=Et
R=R₁=Cyclobutyl
R=R₁=Cyclopentyl
R=R₁=Cyclohexyl.

2. A process for the preparation of a compound of the general formula (A) of claim 1, said process comprising:
   (a) obtaining cedrene epoxide from cedrene,
   (b) converting said cedrene epoxide to a mixture of the epimeric cedrenediols or a mixture of diastomeric cedrenediols (3a/b), and
   (c) reacting the product of step (b) with aliphatic carbonyl compounds under acid catalyzed conditions in an absence of diluent or in an aprotic solvent with the addition of water binding agent(s).

3. A fragrance mixture or perfume oil for perfuming cosmetic or industrial articles, comprising the compound of formula (A) of claim 1 as a fragrance constituent.

* * * * *